United States Patent [19]

Brumbach

[11] Patent Number: 4,660,573
[45] Date of Patent: Apr. 28, 1987

[54] ULTRASONIC LITHOTRIPTOR PROBE

[75] Inventor: Joseph F. Brumbach, Niles, Ill.

[73] Assignee: Fibra-Sonics, Inc., Chicago, Ill.

[21] Appl. No.: 731,772

[22] Filed: May 8, 1985

[51] Int. Cl.⁴ .............................................. A61B 17/00
[52] U.S. Cl. .................. 128/303 R; 128/328
[58] Field of Search ............................ 128/328, 303 R

[56] References Cited

U.S. PATENT DOCUMENTS

| | | | |
|---|---|---|---|
| 2,227,727 | 1/1941 | Leggiadro | 128/328 |
| 3,589,363 | 6/1971 | Banko | |
| 3,618,594 | 11/1971 | Banko | 128/24 A |
| 3,830,240 | 8/1974 | Antonevich et al. | |
| 3,896,811 | 7/1975 | Storz | 128/328 |
| 3,990,452 | 11/1976 | Murry et al. | |
| 4,027,674 | 6/1977 | Tessler | 128/328 |
| 4,030,505 | 6/1977 | Tessler | 128/328 |
| 4,063,557 | 12/1977 | Wuchinich et al. | 604/22 |
| 4,169,984 | 10/1979 | Parisi | 128/305 |
| 4,178,935 | 12/1979 | Gekhman et al. | 128/328 |
| 4,180,074 | 12/1979 | Murry et al. | |
| 4,191,189 | 3/1980 | Barkan | 128/328 |
| 4,425,115 | 1/1984 | Wuchinich | 604/22 |
| 4,428,748 | 1/1984 | Peyman | 604/22 |
| 4,561,438 | 12/1985 | Bonnet et al. | 604/22 |

FOREIGN PATENT DOCUMENTS 2256127 5/1974 Fed. Rep. of Germany ...... 128/328

Primary Examiner—William E. Wayner
Assistant Examiner—David W. Westphal
Attorney, Agent, or Firm—Hill, Van Santen, Steadman & Simpson

[57] ABSTRACT

An improved ultrasonic lithotriptor probe for performing fragmentation and removal of calculi deposits in the kidney and upper ureter wherein high frequency sound waves are utilized to disintegrate the calculi or stones based on placing the probe against the stones and causing them to disintegrate due to the ultrasonic energy. The probe is coupled to a transducer which drives it and the probe is hollow and aspiration is utilized to remove the particles of the stone through the probe. The probe extends into the transducer which prevents the probe from clogging. Also, the end of the probe which engages the stone is provided with a slit so as to prevent it from being clogged by the stone so as to cause the aspiration to be interrupted when the end of the probe extends into the confines of the stone in that the split will allow liquid to pass through the probe and continue to cool it and to remove fragments through the probe.

6 Claims, 5 Drawing Figures

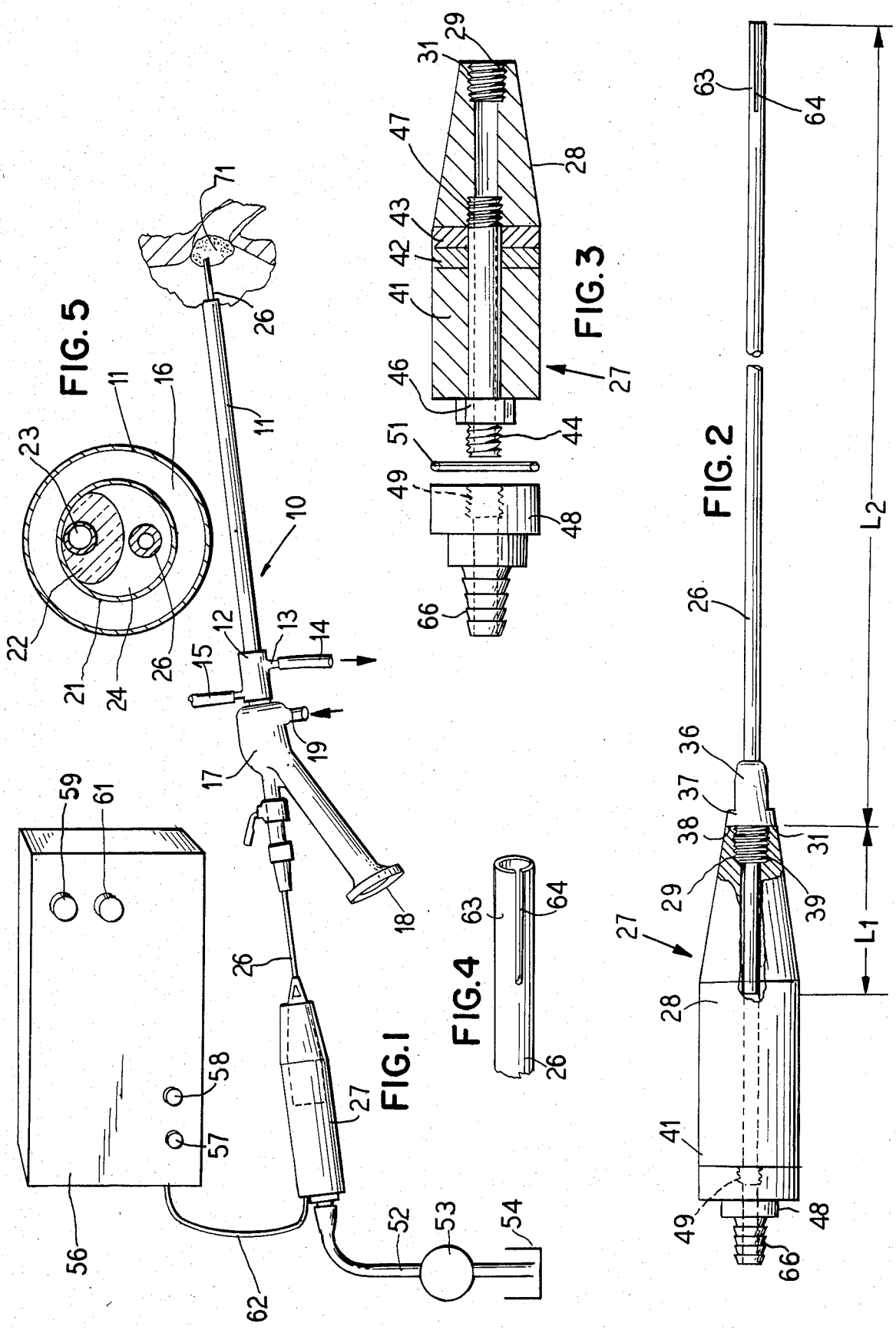

ULTRASONIC LITHOTRIPTOR PROBE

CROSS-REFERENCE TO RELATED APPLICATION

This application is related to patent application of the same inventor entitled "ULTRASONIC NEEDLE FOR EYE SURGERY", identified in the attorney's records as U.S. Ser. No. 748,628 filed 5/8/1985, now abandoned.

BACKGROUND OF THE INVENTION

1. Field of the Invention

This invention relates in general to ultrasonic medical tools and in particular to an improved ultrasonic lithotriptor.

2. Description of the Prior Art

Ultrasonic lithotriptors are known wherein a probe is driven by ultrasound to engage and fragment calculi. Such prior art devices comprised a probe which is a hollow tube that connects to a transducer and terminates at the transducer. Such prior art lithotriptors have a tendency to clog both due to the fact that the tube terminates at the transducer and also because the end becomes embedded into the stone as the probe moves into the stone which prevents aspiration from occurring through the tube.

SUMMARY OF THE INVENTION

The present invention provides an improved ultrasonic lithotriptor which eliminates the disadvantages of the prior art and which prevents the lithotriptor from clogging due to the fact that the end of the tube which is connected to the transducer extends into the transducer sufficiently so that materials within the tube will be pumped from the operating site through the transducer and out the extending end of the tube. The ultrasonic energy causes a pumping action which keeps the tube clear. Additionally, the calculi engaging the end of the tube is formed with one or more slots such that when the tube extends into the calculi, liquid can enter through such slit and pass through the tube thus preventing the tube from becoming clogged and overheated since the fluid flow is uninterrupted and continues through the probe.

Other objects, features and advantages of the invention will be readily apparent from the following description of certain preferred embodiments thereof taken in conjunction with the accompanying drawings although variations and modifications may be effected without departing from the spirit and scope of the novel concepts of the disclosure and in which:

BRIEF DESCRIPTION OF THE DRAWINGS

FIG. 1 is a view illustrating the lithotriptor probe of the invention in use during an operation;

FIG. 2 is a plan view of the lithotriptor probe of the invention;

FIG. 3 is an enlarged detail view of the handpiece of the invention;

FIG. 4, is an enlarged view of the end of the lithotriptor probe; and

FIG. 5 is a sectional view taken on line V—V from FIG. 1.

DESCRIPTION OF THE PREFERRED EMBODIMENTS

FIG. 1 illustrates the operating instrument 10 of the invention which comprises an operating sheath 11 which can be inserted into the body of a patient so as to operate on a calculi or stone 71. The operating sheath has a collar 12 at its outer end to which an irrigant outflow tube 14 can be connected by a pipe 13. A pipe 15 also connects to the sheath 11 to supply irrigant during insertion of the sheath.

A Nephroscope 17 is insertable into the sheath 11 and incorporates a telescope, an eyepiece 18 and fiber optic light system to which is supplied light from a light source to the fiber optic light transmitting media 22 illustrated in FIG. 5. The telescope 18 is connected to an optical telescope channel 23 illustrated in FIG. 5 to provide a magnified view of the stone 71 when the fiber optic light source 22 illuminates it. The Nephroscope 17 also has an opening 24 for the in flow of irrigant to the operating site as illustrated in FIG. 5. A lithotriptor probe 26 can also be inserted through the opening 24 as illustrated in FIG. 5 and is connected to a handpiece 27 which contains an ultrasonic transducer so as to drive the hollow lithotriptor needle 26 to break up the stone. The needle 26 of the present invention extends into the handpiece 27. The transducer has a barb 66 which is connected to a hose 52 which is connected to a pump 53 to supply material from the operating site to a container 54. Irrigating fluid is supplied through the opening 24 from a passage 19 in the Nephroscope 17.

The end of the lithotriptor needle 26 is formed with a slot 64 in its end 63 which engages the stone 71. This is illustrated in detail in FIG. 4. The slot 64 prevents the passageway through the needle 26 from being clogged when the end of the needle 63 is embedded into a stone as it penetrates and breaks it up. In other words, when the end 63 of the needle 26 cuts into a stone during operation the stone would tend to block the removal of particles and liquid from passing through the needle 26 to the container 54. The slot 64 extends a distance sufficient that irrigant fluid can pass through the slot 64 into the needle 63 and to prevent clogging by the stone. In a particular embodiment, the slit 64 extended for ¼ inch from the end of the needle and had a width of 0.010 inches. The flow of irrigant into the needle through the handpiece prevents the handpiece from heating up excessively and reduces the heating. Also, the small slit 64 does not substantially reduce the cutting area of the needle 26.

FIG. 3 illustrates the transducer and handpiece in exploded view and without the needle 26 mounted thereto. The transducer comprises a cylindrical portion 41, a pair of disc-shaped portions 42 and 43 and a truncated conical portion 28. A sleeve 47 is threadedly connected to the conical portion 28 and extends through the portions 41, 42 and 43 and receives a nut 46 on its threaded end as shown in FIG. 3. A disc 51 with an opening fits over the threaded end 44 of the sleeve 47 and handpiece member 48 which is internally threaded with threads 49 is received on the threaded portion 44 to provide the assembled handpiece 27. The needle 26 is formed with an adaptor 36 of generally conical shape which has a an enlarged portion 37 with a shoulder 38 and threaded portion 39 which can be threaded into the transducer portion 28 and threads 29 as illustrated in FIG. 2. The operating portion of the needle is indicated by the dimension L2 in FIG. 2 and the other end of the needle is indicated by dimension L1 and extends through the transducer and the handpiece member 48 as illustrated in FIG. 2.

It is to be noted in the present invention that the end of needle 26 extends beyond the transducer connection point which is defined by the shoulders 31 and 38. The result is that the ultrasonic transducer which drives the cutting end 63 of the needle also drives the end behind the shoulder 31 and, thus, prevents clogging by particles so that they cannot plug up the channel and keeps the channel through the needle clean. In a particular embodiment with a needle designed to operate at a frequency of 30 kHz the dimension L1 was chosen to be $5\frac{3}{4}$ inches and the distance L2 was chosen to be 15 inches. A wavelength at 30 kHz is 3 inches. In another embodiment, the distance L1 was $2\frac{1}{2}$ inches and the dimension L2 was 15 inches. The dimension L1 may be $\frac{1}{4}$ wavelength or n times $\frac{1}{4}$ wavelength. The dimension L2 may be any length up to 10 wavelengths or more and is determined primarily by the desired distance which the lithotriptor must be inserted into the body of the patient.

As illustrated in FIG. 1, electrical leads 62 connect the transducer 28–41 to an ultrasonic generator 56 which has a first knob 57 for controlling the power and a second knob 28 for controlling the frequency. Meters 59 and 61 indicate the power output and the frequency of the generator.

The needle 26 may have different diameters such as 0.072 inches or 0.12 inches. The dimension L1 may be $2\frac{1}{2}$ inches 3 inches, 1.78 inches, 2 5/32 inches, or 2 inches. The dimension L2 may be $21\frac{1}{8}$ inches, 15 5/32 inches, or $14\frac{7}{8}$ inches. All of these combinations work satisfactorily and other dimensions are useable. The main features of the present invention are that the end 66 extends into the transducer and is prevented from clogging by a pumping action and the second feature is the provision of the slit 64 which prevents the end of the needle from being clogged.

Although the invention has been described with respect to preferred embodiments, it is not to be so limited as changes and modifications can be made which are within the full intended scope of the invention as defined by the appended claims.

I claim as my invention:

1. An ultrasonic lithotriptor probe for disintegrating calculi comprising an ultrasonic generator, a handpiece with an ultrasonic motor which is formed with a central opening and connected to said ultrasonic generator, an operating hollow needle connected to said ultrasonic motor at a connection point intermediate its ends such that a first end can be inserted into a body cavity and engage a calculi to disintegrate it, said operating needle having a second end which extends in the opposite direction from said first direction from said connection point between said operating needle and said ultrasonic motor and said first end has a length falling between $\lambda/8$ and 15 inches, where $\lambda$ is the wavelength at the operating frequency of the ultrasonic motor and the length of said second end of said operating needle from the connection point is $m\lambda/4$ where m is an integer.

2. An ultrasonic lithotriptor probe according to claim 1 wherein a tube and suction pump are connected to the second end of said operating needle.

3. An ultrasonic lithotriptor probe according to claim 2 wherein the end of said first end of said operating needle which is remote from said ultrasonic motor is formed with a slit which allows liquid to be sucked into said needle.

4. An ultrasonic lithotriptor probe according to claim 3 including an attaching member connected to said operating needle and formed with a first shoulder and said ultrasonic motor formed with a second shoulder against which said first shoulder can be engaged to position said needle relative to said ultrasonic motor.

5. An ultrasonic lithotriptor probe according to claim 4 wherein said attaching member and said ultrasonic motor are threaded together.

6. A medical instrument according to claim 5 including a hollow operating sheath and a Nephroscope insertable therein and formed with an opening into which said ultrasonic lithotriptor probe can be inserted.

* * * * *